(12) United States Patent
Lee et al.

(10) Patent No.: US 7,354,418 B2
(45) Date of Patent: Apr. 8, 2008

(54) EXPRESS KITS AND CUP LINERS FOR HUMAN MILKING APPARATUS

(75) Inventors: Sung Lee, Elk Grove, CA (US); Bruce McKendry, Benicia, CA (US)

(73) Assignee: L. Jason Clute, Alamo, CA (US)

( * ) Notice: Subject to any disclaimer, the term of this patent is extended or adjusted under 35 U.S.C. 154(b) by 32 days.

(21) Appl. No.: 10/839,968

(22) Filed: May 6, 2004

(65) Prior Publication Data

US 2005/0251089 A1   Nov. 10, 2005

(51) Int. Cl.
*A61M 1/06* (2006.01)
(52) U.S. Cl. .............................. 604/74; 604/75; 604/76
(58) Field of Classification Search .................. 604/74, 604/75, 76, 73, 346; D24/109
See application file for complete search history.

(56) References Cited

U.S. PATENT DOCUMENTS

| | | | |
|---|---|---|---|
| 4,607,596 A | | 8/1986 | Whittlestone et al. |
| 5,100,406 A | * | 3/1992 | Panchula ...................... 604/74 |
| 6,579,258 B1 | | 6/2003 | Atkin et al. |
| 6,663,587 B2 | * | 12/2003 | Silver et al. ................... 604/74 |
| 6,673,037 B1 | * | 1/2004 | Silver ........................... 604/74 |
| 6,706,012 B2 | * | 3/2004 | McKendry et al. ............ 604/74 |
| 6,887,210 B2 | * | 5/2005 | Quay ........................... 600/573 |
| 2002/0198489 A1 | | 12/2002 | Silver et al. |
| 2003/0153869 A1 | | 8/2003 | Ytteborg |
| 2005/0154348 A1 | * | 7/2005 | Lantz et al. ................... 604/74 |

FOREIGN PATENT DOCUMENTS

| | | |
|---|---|---|
| EP | 0 727 234 | 8/1996 |
| EP | 1 034 807 A1 | 9/2000 |
| GB | 2 392 626 A | 3/2004 |
| WO | WO 2004/058330 A1 | 7/2004 |

* cited by examiner

*Primary Examiner*—Kevin C. Sirmons
*Assistant Examiner*—Laura C. Schell
(74) *Attorney, Agent, or Firm*—Greer, Burns & Crain, Ltd.

(57) ABSTRACT

A breast pump includes a pump that produces both vacuum and pulsating pressure, at least one express kit, and hoses or the like for connecting the pump to the express kit. The express kit includes a manifold, a milk collection vessel, a rigid cup and a flexible liner. The liner is made of a pliable material, and includes a funnel and a throat. The inside surface of the funnel, which is between the liner and the cup when the liner is installed, has an optional honeycomb structure that creates a forced space between the liner and the cup, while maintaining some degree of flexibility. At the end of the liner inside the throat, a rigid insert or suitable bond maintains some rigidity inside the throat, supports the liner and creates a seal between the liner and the cup at the throat end of the liner.

4 Claims, 6 Drawing Sheets

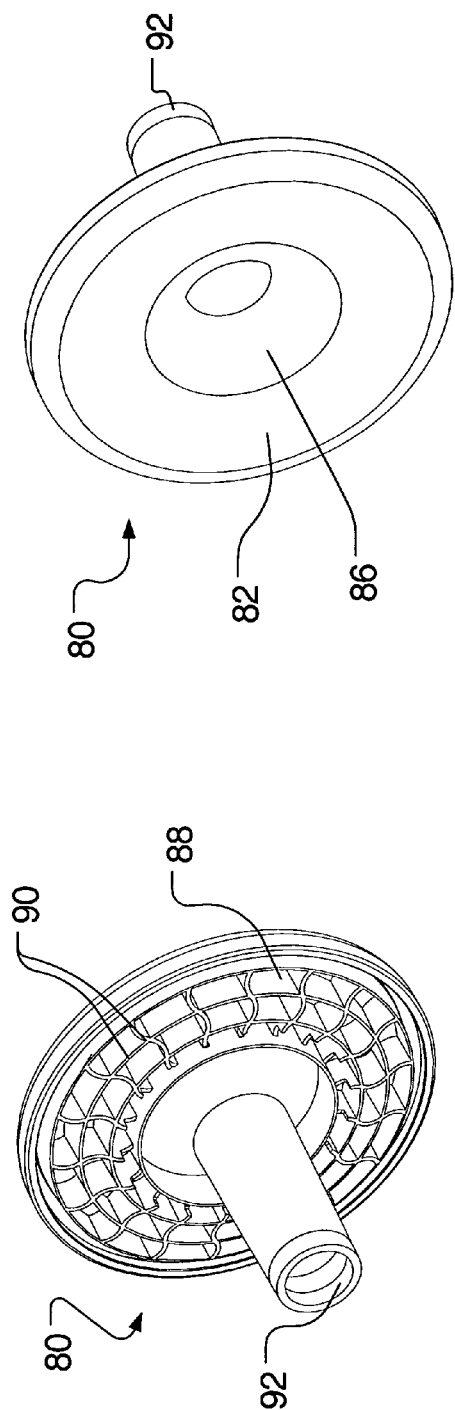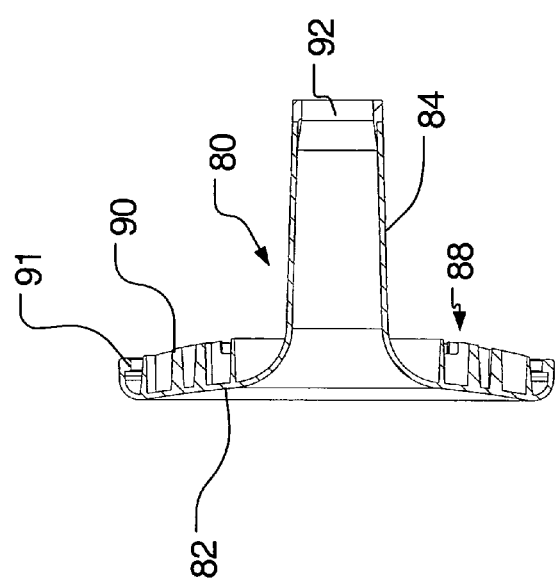

EXPRESS KITS AND CUP LINERS FOR HUMAN MILKING APPARATUS

FIELD OF THE INVENTION

This invention relates to express kits and cup liners for human milking apparatus, and more particularly, to express kits that do not require a separate pad between a breast cup and a cup liner. The invention also relates to cup liners having a honeycomb or the like as part of the underside of the liner, and cup liners that are fixed in a rigid manner inside the throat of the cup or associated manifold.

BACKGROUND OF THE INVENTION

Conventional breast pumps generally include a pump and one or more flanges or collection kits. A typical collection kit includes a manifold, a flange for the breast and a vessel for milk collection. The output of the pump is connected to the manifold such that when vacuum is applied by the pump, milk is drawn from a breast in the flange. The milk is collected in the collection vessel.

Other milking devices have a liner in a cup, and apply pulsation or pulsating pressure to a space or chamber formed between the liner and the cup, as in Whittlestone U.S. Pat. No. 4,607,596. The pulsating action around the outside of the breast stimulates milk production, and increases comfort. However, a pad is used between the cup and the liner. In addition to the expense added by the pad, the pad creates cleaning problems. Thus, there is a need for cups for breast milking devices that eliminate the need for a pad between the liner and the breast cup.

The ends of the liner in Whittlestone et al. are wrapped around the ends of the cup, and a bung is inserted in the small end of the cup for connection to the vacuum source. Among other things, wrapping the liner around the small end of the cup in this manner seals the end of the liner for operating purposes. However, assembly is fairly complicated. Moreover, while the vacuum applied to the breast draws milk from the breast, it also tends to collapse the cup liner around the nipple, which can reduce milk production and cause discomfort. Thus, there is also a need for cups for breast milking devices that have cup liners that are rigidly held along the inside of the throat of the cup, for support and sealing purposes.

SUMMARY OF THE INVENTION

In keeping with one aspect of this invention, a breast milking device includes a pump that produces both vacuum and pulsating pressure, at least one express kit, and hoses or the like for connecting the pump to the express kit. The express kit includes a manifold, a milk collection vessel, a rigid cup and a flexible liner. It does not have a separate pad between the cup and the liner.

The liner is made of a pliable material, and includes a funnel, a throat, and a transitional portion between the funnel and the throat. The surface of the funnel between the liner and the cup when the liner is installed has a honeycomb structure that creates a forced space between the liner and the cup, while maintaining some degree of flexibility. At the end of the liner inside the throat, a rigid insert or suitable bond maintains some rigidity inside the throat, supports the liner and creates a seal between the liner and the cup at the throat end of the liner.

BRIEF DESCRIPTION OF THE DRAWINGS

The above mentioned and other features of this invention and the manner of obtaining them will become more apparent, and the invention itself will be best understood by reference to the following description of an embodiment of the invention taken in conjunction with the accompanying drawings, in which:

FIG. 4a is a perspective view of the cup liner used in the express kit of FIG. 2;

FIG. 4b is another perspective view of the liner of FIG. 4A, showing the front side of the liner;

FIG. 4c is a cutaway view of the liner of FIG. 4a, taken through the midsection;

DETAILED DESCRIPTION

Figure 1:
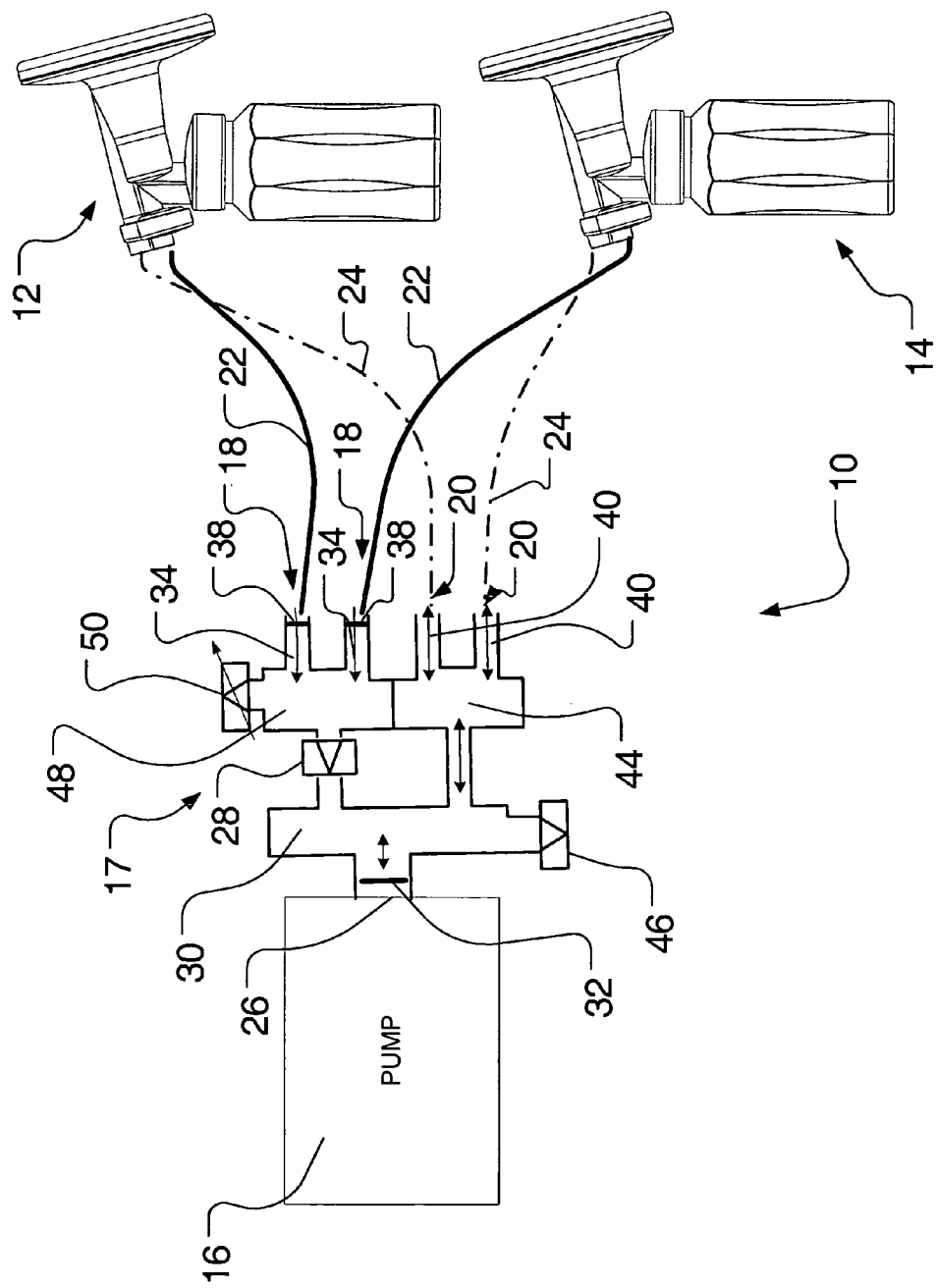
FIG. 1 is a diagram of one embodiment of a breast pump made in accordance with the principles of this invention.

As seen in FIG. 1, a breast pump 10 has two express kits 12, 14, a pump 16 and an external adapter 17.

The pump 16 can be a diaphragm pump, piston pump, or any other suitable type of pump. The pump 16 typically produces an intermittent vacuum or negative pressure. The vacuum output of the pump provides an input to the adapter 17, which in turn produces fairly constant vacuum outputs 18 and pulsating or alternating pressure at outputs 20. The pulsating or alternating pressure is separately provided to massage the breast and relieve congestion brought to the front of the breast by the application of the vacuum. Hoses 22 connect the outputs 18 to the express kits 12, 14, and hoses 24 (shown in broken lines for illustrative purposes) connect the outputs 20 to the express kits 12, 14.

The pump itself could produce both outputs 18, 20 directly, as in Whittlestone U.S. Pat. No. 4,607,596, the contents of which are incorporated by reference in their entirety, or the adapter kit 17 can be used to produce the outputs 18, 20 from a pump that only produces vacuum, as shown in FIG. 1 and described in U.S. patent application Ser. No. 10/625,246, filed Jul. 23, 2003, entitled Adapter For Human Breast Pumps, the contents of which are incorporated by reference in their entirety.

Shown schematically in FIG. 1, the adapter 17 is an air circuit that includes an input 26 that feeds a one-way valve 28 through a chamber 30. A filter 32 may be placed in the input path, if desired, to protect against contamination. The output of the one-way valve 28 in turn produces the outputs 18, the airflow being as shown by arrows 34. One output 18 could be plugged or eliminated if a single breast cup assembly were used. Filters 38 are used, if desired.

The input 26 also produces the outputs 20, the airflow being as shown by arrows 40 through the chamber 44. The chamber 30 has a one-way check valve 46 that exhausts positive pressure from the chambers 30 and 44.

Pressure at the input 26 is bi-directional, i.e., both positive (pressure) and negative (vacuum), or intermittently negative, and it is transmitted directly to the outputs 20 when two breast cup assemblies are used. A single breast cup configuration would only need one output 20. The valve 28 converts the bi-directional or intermittent pressure at the input 26 into a uni-directional vacuum. A vacuum reserve chamber 48 can be provided, if desired, as can a vacuum control valve 50. The valve 50 can be a needle valve or other suitable device that provides vacuum adjustment.

Figure 2:
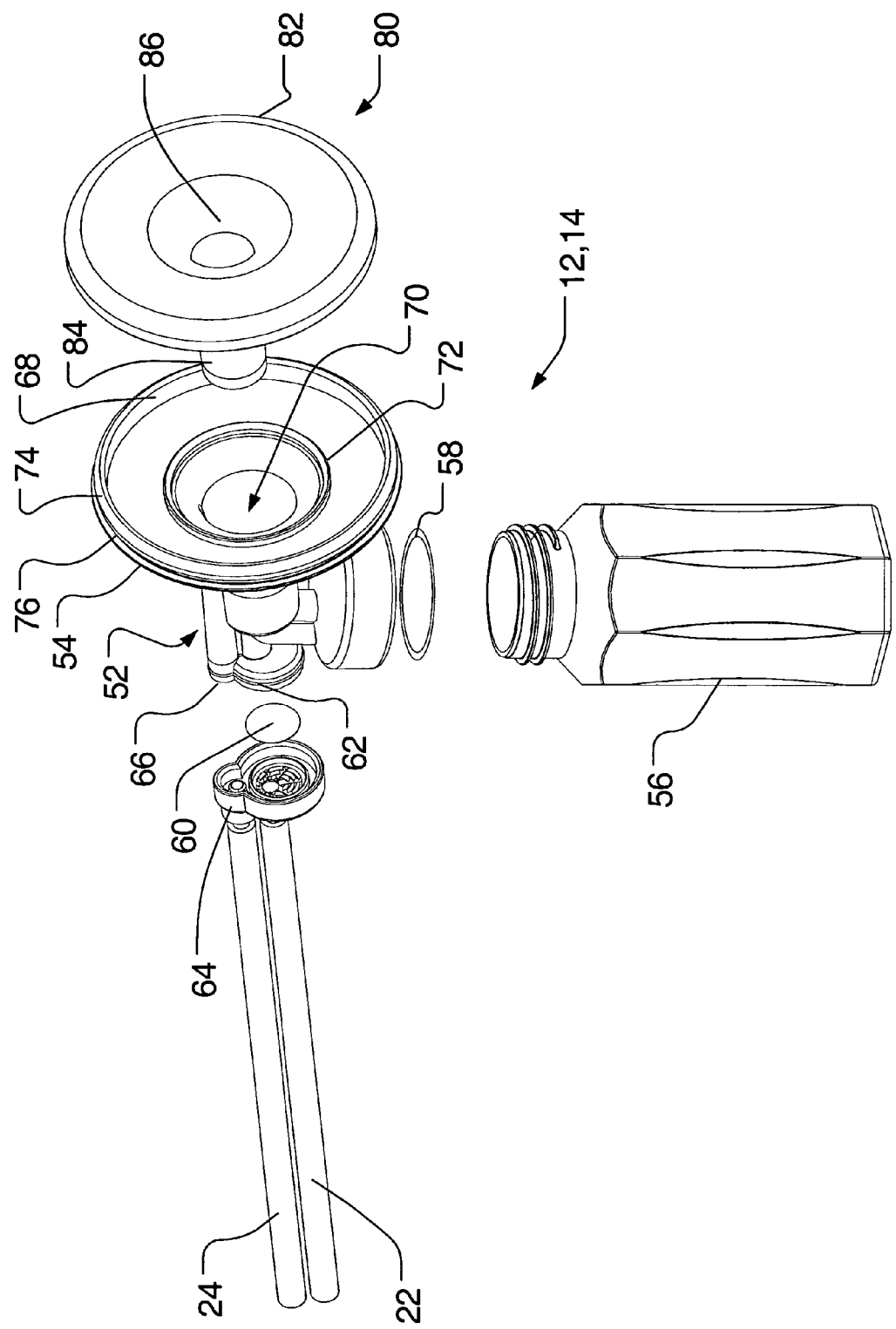
FIG. 2 is an exploded view of one embodiment of an express kit used in the pump of FIG. 1.

The express kits 12, 14 (FIG. 2) have a manifold 52, a breast cup 54 and a milk collection vessel 56. The breast cup 54 can be integral with or separate from the manifold 52.

The milk collection vessel 56 is typically removable. A washer 58 may be provided between the manifold 52 and the milk collection vessel 56, if desired, or the washer 58 may be over-molded in the manifold at manufacture.

A filter 60 may be provided between the vacuum introduced by the hose 22 and a vacuum inlet 62 of the manifold 52, if desired. If the filter 60 is used, a cap 64 can be provided for the manifold 52. The cap 64 can be press fit to the manifold input 62, or connected in any other suitable way. The cap 64 also includes appropriate fittings to pass the pressurized air in the tube 24 to a pressure input 66 in the manifold 52.

Generally speaking, the manifold 52 and breast cup 54 form a funnel 68 and an interior throat 70. the breast cup 54 has a first opening 54a (FIG. 3) at an end of the cup funnel section 68 opposite to the cup throat 70, and a second opening 54b at an end of the cup throat 70 opposite to the cup funnel section 68. The transition from the funnel 68 to the throat 70 can be gradual. The funnel 68 can include an interior raised portion 72, if desired. In addition, an outer lip or rim 74 is provided near the outer edge of the funnel portion 68, with an indentation or groove 76.

A liner 80 is also provided for each express kit 12, 14. The liner 80 has a liner funnel 82 and a liner throat 84, and a transitional portion 86 between the funnel 82 and the throat 84. The liner has generally uniform thickness, to produce a non-peristaltic action when the liner is moved under pressure.

The vacuum applied to the breast in the liner throat 84 (through a vacuum input 85 shown in FIG. 3) draws the liner inwardly towards the breast. Pulsating pressure can be applied to the outside of the liner by directing the output 20 of the adapter 17 through an inlet 87 (FIG. 3) to a chamber 89 formed between the manifold 52 and/or breast cup 54 on one side, and the liner 80 on the other side.

The liner releases or moves away from the breast when the pulsating pressure is more negative than the vacuum at the breast. In other words, liner wall movement occurs when the difference or differential between the vacuum at the breast and the vacuum produced by the pulsation source is such that the pulsation source vacuum is greater, (i.e., more negative) than the vacuum at the breast.

The inside or back of the liner 80 is shown in FIGS. 4a and 4c, and the front of the liner is shown in FIG. 4b. The outer edge of the funnel portion 82 has a lip 91. The funnel portion 82 also has a honeycomb structure 88 that includes a plurality of raised lips 90 that extend generally in both the radial and axial directions.

The liner 80 can have a rigid insert 92 at the outer end of the liner throat 84. The insert 92 can be plastic or any other suitable material, and it can be bonded or molded into the liner when the liner is molded. The insert 92 can be wholly within the liner, or it can extend beyond the open end of the liner.

Figure 3:
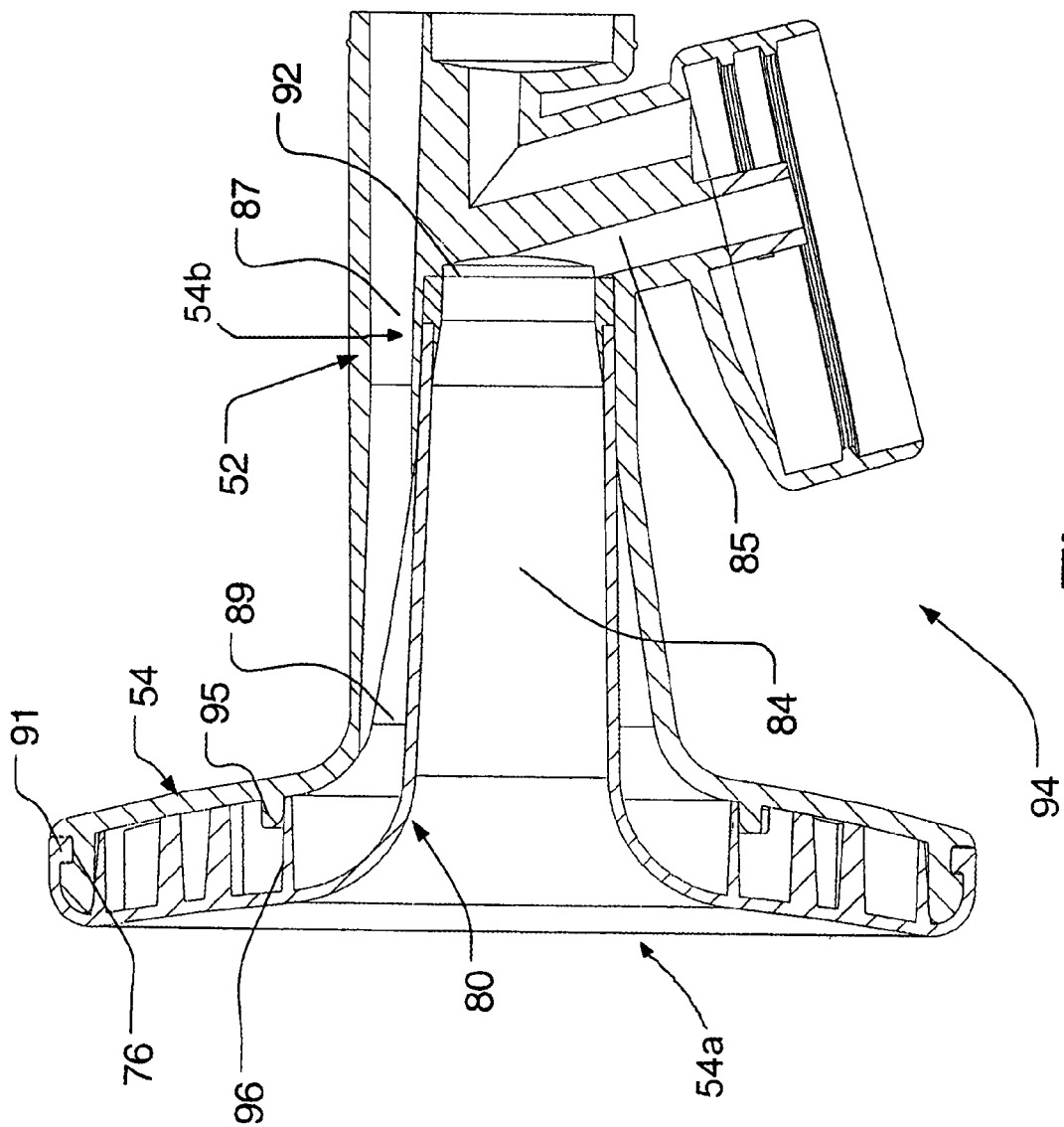
FIG. 3 is a sectional view of the cup liner used in the express kit of FIG. 2, shown in a cup and manifold.

Among other things, FIG. 3 shows how the liner is installed in an integrated cup and manifold 94. The end 91 is engaged in the groove 76 in the cup, and the insert 92 locates the liner against the wall of the manifold/cup 94, creating a seal sufficient to conserve a vacuum in the liner in use. The liner can also be bonded to the cup/manifold, if desired. A suitable bonding agent can be used at or near the groove 76 and at the other end at or near the insert 92.

Figure 6:
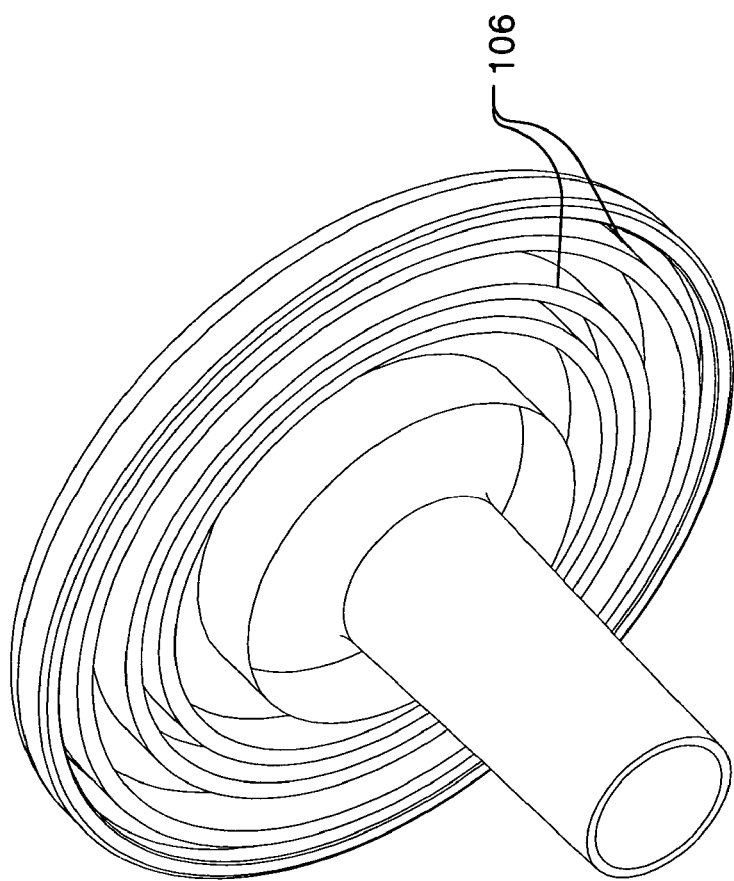
FIG. 6 is another alternate embodiment of the liner of FIG. 1.

An alternate embodiment of the cup liner is shown in FIG. In FIG. 6, the honeycomb structure is in the form of side by side open cylindrical chambers 104, where in FIG. 4a the honeycomb is in the shape of rectangles and/or trapezoids. Squares could also be used, if desired.

Another embodiment of the cup liner is shown in FIG. 6. In that embodiment, the honeycomb structure is a plurality of circular lips 106, without radial structure.

The cup liner can be manufactured by any suitable process, such as liquid injection molding if silicone is used, or injection molding with the use of TPE, for example.

The liner 80 (FIG. 2) is installed by sliding the liner throat 84 into the cup throat 70, and folding the liner lip 91 (FIG. 3) over and placing it into the groove 76. The insert 92 (FIG. 4a) in the open end of the liner substantially seals the end of the liner to the corresponding inside surface of the cup.

Returning now to FIGS. 1 and 2, vacuum is drawn inside of the throat of the liner, and pulsating pressure is applied to a chamber formed between the liner and the cup. The honeycomb structure inside the liner creates a forced space between the liner and the cup, while retaining some flexibility for comfort. Moreover, a ridge 95 in the cup and a lip 96 in the liner can be configured to create a partial seal inside the pulsating chamber, which reduces the effective size of the chamber, if desired.

The pulsating pressure is preferably applied at 41-65 cycles per minute, with a pressure differential of about 0.5-2.0 Hg. The relationship of time between the open and closed positions can be expressed as a ratio. The pulsation ratio is preferably between about 20% and 80% open of the total of each pulsation cycle (i.e., time open/total time of each cycle).

While the liners described have a honeycomb structure of some kind, an express kit can be made with a liner that does not have a honeycomb structure, a pad or other structure between the liner and the cup.

The advantages of the invention are now apparent. The honeycomb inside the liner maintains a flexible cushion between the liner and the cup, without the need for additional parts, such as pads or the like. In fact, the pad can be eliminated without having a honeycomb in the liner. In addition, the plastic insert or suitable bond at the throat end of the liner sufficiently seals the end of the liner without wrapping it around another part, and provides rigidity to the liner so that it does not collapse in use, pinching the nipple.

While the principles of the invention have been described above in connection with specific apparatus and applications, it is to be understood that this description is made only by way of example and not as a limitation on the scope of the invention.

What is claimed is:

1. An express kit for a breast pump, comprising: a manifold; a milk collection vessel releasably secured to the manifold; a breast cup secured to the manifold and integral with or separate from the manifold, the breast cup having a cup funnel section and a cup throat; and a liner in the breast cup, the liner having a funnel portion, a throat portion and a transitional portion between the funnel portion and the throat portion; wherein the liner forms a pulsation chamber with the cup, without a pad or other device intervening between the liner and the cup; the liner has an integral honeycomb structure on the surface of the funnel portion of said liner between the liner and the cup, the honeycomb structure creating a forced space between the funnel portion of the liner and the cup, only in the funnel portion of the liner, the honeycomb structure being an outwardly extending structure that prevents any portion of the liner funnel surface in the forced space from contacting the breast cup; and the breast cup has a ridge located between the funnel portion and throat portion of the breast cup, and the liner has a lip located at a junction of the honeycomb structure and the transition portion of the liner, which ridge and lip are configured to create a partial seal inside the said pulsation chamber.

2. The express kit of claim 1, comprising means for sealing the liner to the funnel section at a first opening and to the throat portions of the manifold and/or breast cup.

3. The express kit of claim 2 wherein said sealing means comprises a rigid ring secured to said liner.

4. The express kit of claim 2 wherein said sealing means comprises an adhesive bond.

* * * * *

UNITED STATES PATENT AND TRADEMARK OFFICE
CERTIFICATE OF CORRECTION

| | |
|---|---|
| PATENT NO. | : 7,354,418 B2 |
| APPLICATION NO. | : 10/839968 |
| DATED | : April 8, 2008 |
| INVENTOR(S) | : Sung Lee |

It is certified that error appears in the above-identified patent and that said Letters Patent is hereby corrected as shown below:

Col. 3, line 22, delete "the" and insert --The--.

Figure 5:
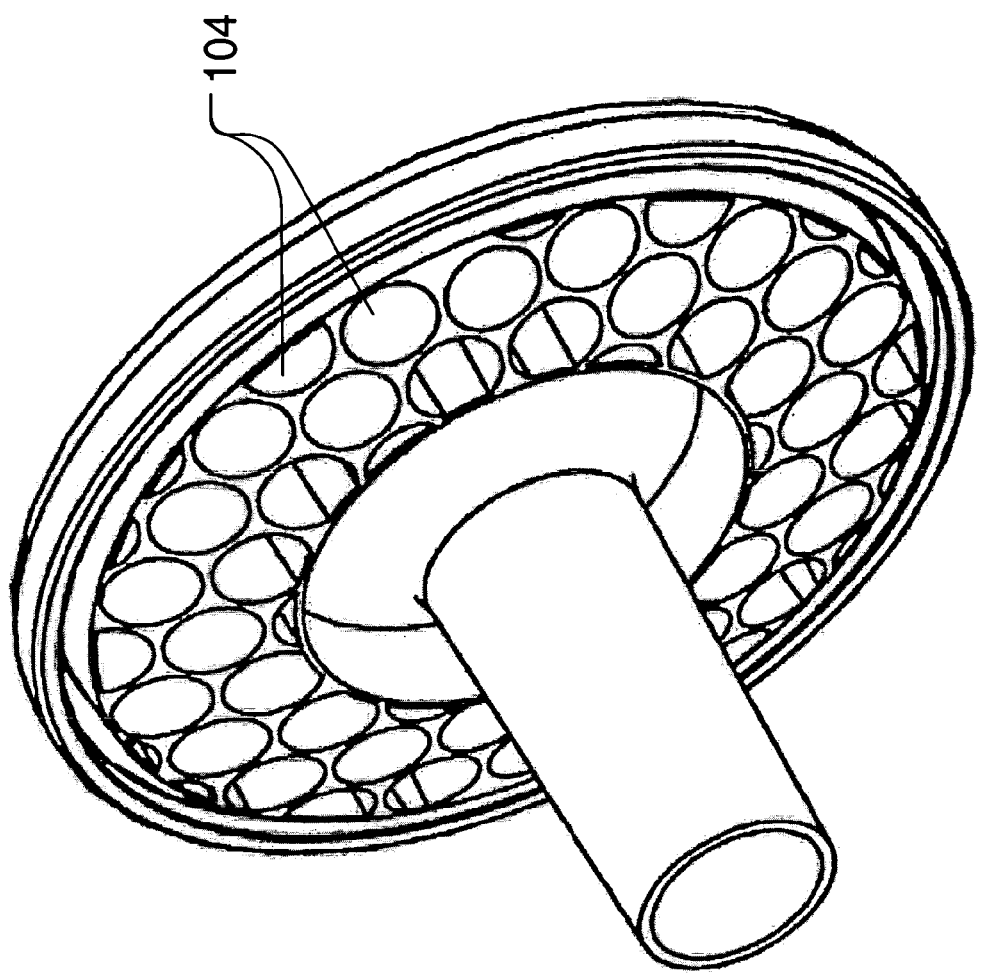
FIG. 5 is a perspective view of an alternative embodiment of the liner in the express kit of FIG. 1.

Col. 4, line 4, delete "FIG." and insert --FIG. 5--.

Col. 4, line 5, delete "FIG. 6" and insert --FIG. 5--.

Signed and Sealed this

Third Day of February, 2009

JOHN DOLL
*Acting Director of the United States Patent and Trademark Office*